United States Patent [19]

Moeremans et al.

[11] Patent Number: 5,279,792
[45] Date of Patent: Jan. 18, 1994

[54] STAINING KIT FOR PROTEINS AND NUCLEIC ACIDS

[75] Inventors: Marc K. J. J. Moeremans, Mol; Guido F. T. Daneels, Gierle; Marc C. De Raeymaeker, Mechelen; Jan R. De Mey, Turnhout, all of Belgium

[73] Assignee: Janssen Pharmaceutica N.V., Beerse, Belgium

[21] Appl. No.: 710,248

[22] Filed: Jun. 3, 1991

Related U.S. Application Data

[60] Continuation of Ser. No. 462,018, Jan. 8, 1990, abandoned, which is a division of Ser. No. 744,091, Jun. 12, 1985, Pat. No. 4,920,059.

[30] Foreign Application Priority Data

Jun. 22, 1984 [GB] United Kingdom ............... 8415998

[51] Int. Cl.$^5$ ............... G01N 1/30; G01N 21/00; G01N 33/48; C12Q 1/70
[52] U.S. Cl. ............... 422/61; 436/86; 436/87; 436/88; 436/94; 436/164; 436/169; 435/6; 424/3; 424/7.1
[58] Field of Search ............... 435/6; 436/86, 87, 88, 436/94, 164, 169; 422/61; 424/3, 7.1

[56] References Cited

U.S. PATENT DOCUMENTS 4,416,998 11/1983 Adams et al. ............... 422/61 X

FOREIGN PATENT DOCUMENTS 0205855 11/1983 Japan .

OTHER PUBLICATIONS

Surek et al, Biochem. Biophys. Res. Com., vol. 121, No. 1, pp. 284–289, May 31, 1984.

Holgate et al, J. Hist. Cyt., vol. 31, No. 7, pp. 938–944, 1983.

DeBlas et al, Anal. Biochem., vol. 133, pp. 214–219, 1983.

Primary Examiner—James C. Housel
Assistant Examiner—Rachel Heather Freed

[57] ABSTRACT

A kit for staining proteins and nucleic acids wherein the stain is a suspension of colloidal metal particles and the proteins and nucleic acids are visualized as a colored signal localized at the binding site of the colloidal metal particles to the proteins or nucleic acids or quantitatively determined at this site following art-known spectrophotometric procedures.

1 Claim, No Drawings

STAINING KIT FOR PROTEINS AND NUCLEIC ACIDS

This application is a continuation of application Ser. No. 07/462,018, filed Jan. 8, 1990, now abandoned, which is a division of application Ser. No. 06/744,091, filed Jun. 12, 1985, now U.S. Pat. No. 4,920,059.

Gel electrophoretic techniques are essential tools for analyzing complex mixtures of polypeptides and nucleic acids. Applied to proteins the high resolution of these techniques is also exploited for testing the binding activities of antibodies, lectins and various proteins to specific components of such mixtures. The techniques for such an analysis are called overlay assays. They are preferentially performed on electrophoretograms transferred to immobilizing matrices, such as nitrocellulose or nylon based membranes (protein or nucleic acid blots). For proteins, this subject has recently been reviewed by Gershoni and Palade (Anal. Biochem. 1983, 131, 1–15). The sensitivity of the various overlay techniques is very high: going down to sub-nanogram amounts. This has created the need for a sensitive staining method in order to make a direct correlation between the total electrophoretogram and detected bands in the overlay possible. Stains like Coomassie blue, amido black and fast green do not match the high sensitivity of overlay techniques. For nylon based membranes such as Zeta-probe (Bio-Rad), no useful staining method is available. The common practice is to stain the separated proteins in a duplicate polyacryl amide gel with a silver staining method. However, due to shrinkage of the gel in the blotting buffer (Towbin et al., Proc. Natl. Acad. Sci. 1979, 76, 4350–4354), the size of the blot and the gel after staining become different, making such a direct correlation difficult. More important, it does not give information on the blotting accuracy and efficiency which may be problematic for certain proteins. An indian ink staining method (Hancock and Tsang, Anal. Biochem. 1983, 133, 157–162) has been described which only works on nitrocellulose protein blots, but is more sensitive than the other protein staining methods and easy to use. The contrast provided by this method, however, is not very sharp.

The methodology of analyzing complex mixtures of nucleic acids is described e.g. in Devos et al., J. Mol. Biol., 128, 595–619 (1979). Staining of nucleic acids is usually carried out with ethidium bromide. Although the sensitivity of the method is high, it has the serious disadvantage of not being applicable to blotting membranes or to denatured DNA.

The invention described hereafter deals with staining of proteins or nucleic acids in or on all kinds of supports. Nucleic acids in this respect comprise both ribonucleic and deoxyribonucleic acids. The essential point of the present invention is the use as the stain of colloidal metal particles which are adjusted to an optimal pH and concentration. The term Ocolloidal metal particles used in this connection is meant to include dispersions of particles, preferably sols, consisting of a metal, a metal compound or nuclei coated with a metal or metal compound. Colloidal metal particles can be prepared following art-known procedures, such as have been described for preparing suspensions or sols of gold, silver, platinum or iron hydroxide and the like.

The invention is based on the surprising finding that optimally concentrated and pH adjusted colloidal metal particles bind with high affinity and selectivity to the proteins and nucleic acids and produce a clearly contrasted color characteristic for the colloidal metal particles used.

Optionally, the signal can be modified and/or enhanced by further physical development or by transforming the colloidal metal into metal ions and subsequently using art-known color identification methods of metal ions. For example, $Fe^{3+}$ ions of colloidal iron hydroxide form stable complexes with, for example, ferrocyanide salt complexes (e.g. $K_4Fe(CN)_6$, potassium ferrocyanide), which complexes are strongly colored.

Thus, where the stain is a colloidal suspension of iron hydroxide, the final detection of the stain may be effected by hydrolyzing the iron hydroxide with an acid and treating the thus formed ferric salt with a ferrocyanide salt complex.

Examples of colloidal metal particles that will bind to proteins and nucleic acids when adjusted to the optimal pH and concentration are the metals platinum, gold, silver and copper, and the metal compounds, for example, gold, silver, platinum, iron, or copper compounds, such as, silver iodide, silver bromide, copper hydrous oxide, iron oxide, iron hydroxide or hydrous oxide, aluminium hydroxide or hydrous oxide, chromium hydroxide or hydrous oxide, vanadium oxide, arsenic sulfide, manganese hydroxide, lead sulfide, mercury sulfide, barium sulfate and titanium dioxide. Colloids consisting of nuclei, coated with the above mentioned metals or metal compounds can also be used. The particles have similar properties as the metal or metal compound colloids, but size, density and metal content can be optimally combined. In general, all colloidal metal particles or metal compounds which can be adjusted to the optimal PH for protein binding and which give a color intensity in protein staining, sufficient to be observed by the naked eye, can be used. Preferably, the sensitivities are equal or superior to those obtained with the metals gold and silver.

For the staining of proteins, particularly good results are obtained with gold, silver and iron hydroxide colloids. Colloidal iron hydroxide has proven particularly useful for the staining of nucleic acids.

The particle size of the colloidal metal or metal compound particles is preferably comprised between 1 to 100 nm. The appropriate pH is preferably the pH at which binding is maximal and the most intense color is obtained. Maximal binding occurs when the proteins and the colloidal metal particles have opposite net charges. This is different from the known methods for making protein-coated colloidal metal particles used as probes in histochemistry and biochemistry. In this field, the proteins are adsorbed onto the colloidal metal particles at a pH close to the pi of the protein. Adjustment of the PH can be achieved in any of the usual ways. Addition of a stock buffer to about a 10 mM final concentration to the colloidal metal particles is a preferred method.

The appropriate concentration of the colloidal metal particles is one that gives full color saturation within practical incubation times (from a few minutes to one day). It can be obtained by choosing the proper concentrations of the raw materials with which they are prepared, or by dilution or concentration by art-known methods.

The supports in or on which proteins and nucleic acids can be stained according to the present invention can be of various kinds and comprise, for example, gels, in particular those employed for protein and nucleic acid separation by chromatography, electrophoresis or used as supports for any of the art-known immunochemical procedures such as immunodiffusion, radioimmunodiffusion, immunoelectrophoresis, counter immuno-electrophoresis or immunofixation; and immobilizing matrices used as supports for overlay techniques for proteins or nucleic acids (e.g. hybridization techniques). The proteins and nucleic acids can be immobilized by direct absorption and/or covalent binding.

Examples of such gels on which the staining method according to the invention can be successfully applied include, for example, agarose and cellulose acetate gels.

Immobilizing matrices are meant to include any kind of polymeric material on which proteins or nucleic acids can be immobilized, in particular materials onto which proteins or nucleic acids are transferred from separation media by a process generally referred to as blotting. Examples of such matrices are nitrocellulose, nylon (e.g. a polyhexamethylene adipamine), cellulose acetate and various modified cellulose acetates like diazobenzyloxymethyl (DBM)- or diazophenylthioether (DPT)-modified cellulose paper.

It is advantageous to wash the supports before the staining procedure. This washing is intended to remove adherent interfering materials like, for example, polyacrylamide gel particles and residual SDS (sodium dodecyl sulfate), if SDS-PAGE (polypcrylamide gel electrophoresis) has been used first. Such washing of the immobilized matrix may be effected by contacting it with a buffer solution or water optionally supplemented with at least one substance which promotes the staining specificity defined as specific binding of the colloidal or metal compound particles to the proteins or nucleic acids and the absence of such specific binding on those parts of the immobilizing matrix where no protein or nucleic acids are immobilized. It is also found to be advantageous to add a detergent to the colloidal metal particles, before or after adjusting the pH. Such detergents are herein exemplified by Tween 20 (polyoxyethylene sorbitan monolaurate), Tween 80 (polyoxyethylene sorbitan mon-oleate), Triton X-100 (octyl phenoxy polyepoxy ethanol) and myristyltrimethyl ammonium bromide. It will be understood by one skilled in the art that similar detergents, i.e., surface active substances, can be used as well. The detergent added to the colloidal metal particles may also be employed to promote the specific binding of the colloidal metal particles to the protein or nucleic acids.

In comparison with existing staining techniques, the method according to the invention is distinctly superior, particularly in view of its substantially higher sensitivity. As a result, it can be used to detect proteins and nucleic acids in extremely low amounts, which in many circumstances is a highly desirable objective. As mentioned above, such high sensitivity is essential for the adequate staining of protein blots, but it has great advantages too in connection with the direct visualization of proteins or nucleic acids in or on other supports, in particular gels, like, for example, separation media, e.g. electrophoretograms. in this respect, the invention makes it possible to visualize protein separations of samples with a very low protein content, for example, certain biological liquids like cerebrospinal fluid (CSF). CSF contains only very low amounts of protein and with the usual analytical and diagnostic techniques, concentration of the fluid, prior to carrying out electrophoretic protein analysis is needed and hence, relatively large samples are needed. A limited amount only can be obtained from one puncture and because of the trauma to the patient and because of the effort and skill demanded in obtaining good specimens, every measure which will reduce the volume needed for analysis is considered a definite advantage, making the technique, more than at present, available for routing analysis and diagnosis.

The fact that preliminary concentration or enrichment of the sample can be avoided is an important improvement, facilitating diagnostic methods applied to various fluids like serum and urine.

Consequently, the method according to the invention provides a considerable improvement of the existing techniques for the diagnosis of a number of metabolic disturbances and diseases, such as, for example, the detection of brain tumors by CSF analysis and myeloma by analysing urine samples. Hence, the present invention is one with great utility, particularly in clinical diagnosis.

The result of the staining operation can be used for both qualitative and quantitative evaluations. Qualitative evaluation is usually done by mere visual inspection. Quantitative measurements are usually carried out with spectroscopic techniques such as reflectometry or densitometry. When using a densitometric technique, it may be necessary to make the support first transparent by treatment with appropriate solvents, e.g. xylene.

The process of the invention comprises the steps of:
i. contacting a properly washed and, if desired, subsequently air-dried protein or nucleic acid support for a given time, with a sufficient concentration of colloidal metal particles suspended in a medium, preferably containing a detergent that does not interfere with protein or nucleic acid binding, like for example 0.1% of the non-ionic detergent Tween 20, and appropriately pH adjusted. Optionally, the optical signal formed by the colloidal metal particles may be enhanced by appropriate enhancers such as physical developers, for example, silver- or gold-containing compounds, or modified and/or enhanced by art-known color identification methods of metal ions after transformation of the colloidal metal into a metal ion;
ii. reading the colored signal produced by and characteristic for the bound colloidal metal particles with the naked eye or using art-known spectrophotometric techniques such as densitometry.

In a specific embodiment, the invention comprises a process for staining proteins and nucleic acids in a gel support characterized in that the stain is a suspension of the metal particles and the protein and nucleic acids are visualized as a colored signal localized at the binding site of the colloidal metal or metal compound particles to the proteins and nucleic acids as quantitatively determined at this site following art known spectrophotometric procedures. Such a process may include the steps of contacting the gel support optionally after fixing the proteins or the nucleic acids with art known fixing solutions, with the staining suspension containing colloidal metal particles, preferably a salt, in an appropriate medium, adjusted to an appropriate concentration and pH, and supplemented with at least one substance with promotes the specific binding of the colloidal metal particles to the protein or nucleic acids; then optionally washing the gel support; and then detecting the colored signal at the reaction site in the gel support. In such a process, the washing of the gel support may be effected by contacting it with a buffer solution or water optionally supplemented with at least one substance which promotes the staining specificity defined as specific binding of the colloidal metal particles to the proteins and nucleic acids and the absence of such binding on those parts of the gel support where no proteins or nucleic acids are located. Such a substance which promotes the staining specificity may be a detergent, which may be selected from the group consisting of Tween 20, Tween 80, Triton X-100, and myristyltrimethylammonium bromide.

In a further embodiment, the invention comprises a kit for use in staining and detecting proteins or nucleic acids. Such a kit comprises: i) a staining suspension comprising a sol of metal particles, as described herein, adjusted to an appropriate concentration and appropriate pH; and ii) a substance which promotes specific binding of the colloidal metal or metal compound particles to the proteins or nucleic acids. The kit may further comprise a reagent for modifying and/or enhancing the signal originating from the colloidal metal or metal compound, as described herein.

The invention is further illustrated by the following examples which are not intended to limit the scope thereof.

EXAMPLE I

Staining of a concentration range of proteinaceous molecular weight markers transferred to a nitrocellulose membrane with colloidal gold particles. Materials used include a colloidal gold sol, comprising particles of 20 nm mean diameter (supplier: Janssen Life Sciences Products, Beerse, Belgium) and nitrocellulose sheets (0.45 $\mu$), Tween 20 and High Molecular Weight (HKW) standards (all from Bio-Rad). The HMW standards consisted of myosin (200 kDa), $\beta$-galactosidase (116,5 kDa), phosphorylase B (92.5 kDa), bovine serum albumin (66.2 kDa) and ovalbumin (43 kDa), all at approximately 2 mg/ml as indicated by the manufacturer. The HMW standards were separated by SDS-gel electrophoresis according to Laemmli, O. K. (Nature 1970, 227, 680–685) on two 7.5% polyacrylamide gels. A serial dilution (1000-3.5 ng per polypeptide band) was loaded in 9 wells of each 10 well-gel. The last well was loaded with sample buffer alone. After the run, one gel was stained with a silver staining method (Morissey, J. H., Anal. Biochem. 1981, 117, 307-310). The separated proteins of the other gel were electrotransferred to nitrocellulose paper (Towbin et al., Proc. Natl. Acad. Sci. 1979, 76, 4350-4354). The blot was washed in a large Petri-dish with phosphate buffered saline (PBS) (without $ca^{2+}$ and $Mg^{2+}$, pH 7.2) containing 0.3 & V/V Tween 20, (PBS-TW) at 370° C. and 3×15 minutes with PBS-TW at room temperature. The washed blot was rinsed in excess water.

The rinsed blot was incubated with colloidal gold stain, prepared as follows (for 100 ml):
75 ml colloidal gold (G20, Janssen Life Sciences Products)
5 ml 2% Tween 20 in $H_2O$
20 ml 50 mM citrate buffer PH 3.0.

The Tween 20 and gold sol was well mixed before addition of the buffer.

Incubation lasted four hours. The stained blot was rinsed in $B_2O$ and air-dried. Protein bands detected by the colloidal gold stain appeared as red bands. The sensitivity of the staining was in the same range as silver staining of proteins in polyacrylamide gel. The detection limit was estimated at about 250 pg/mm².

EXAMPLE II

Staining of molecular weight markers transferred to a nitrocellulose membrane with colloidal silver particles. Colloidal silver particles were prepared according to Frens and Overbeek (Koll. Z. U. Z. Polym. 1969, 223, 922–929). HMW standards, nitrocellulose sheets and Tween 20 were the same as in example I. 12.5 $\mu$l of HMW standard stock solution were diluted in 500 $\mu$l sample buffer, boiled for 3 minutes and run in a one-well 7.5% polyacrylamide gel as in example I.

Electrotransfer, washing with PBS-TW and rinsing with water was done as in example I. One strip, 4 mm wide, was incubated with the gold stain. A second strip was incubated with colloidal silver stain, prepared as follows:
75 ml colloidal silver ($A_{394\ nm}$+1.0 when diluted one hundred times in water)
5 ml 2% Tween 20 in $H_2O$
20 ml 50 mM citrate buffer, pH 3.0.

The Tween 20 and silver sol are well mixed before addition of the buffer. Incubation lasted four hours. The stained blot was rinsed in $H_2O$ and air-dried. Protein bands detected by the colloidal silver stain appeared as brown to black bands. The sensitivity was in the same range as the colloidal gold stain.

EXAMPLE III

Staining of molecular weight markers transferred to a Zeta-probe membrane with colloidal iron hydroxide particles. Colloidal iron hydroxide was made according to Bradburry et al., Histochem. J. 1970, 2, 263-274. 200 ml 0.5M $FeCl_3$ ($6H_2O$) were dropwise added to 800 ml boiling water, under continuous stirring. The colloid was dialysed against several changes of $H_2O$. HMW standards were the same as in example I. As a blotting medium was used Zeta-probe, a nylon matrix (a polyhexamethylene adipamine, referred to as Nylon 66) modified by the introduction of numerous tertiary amino groups during manufacturing (supplier: Bio-Rad). TritonX-100 (octyl phenoxy polyethoxy ethanol) (supplier: Sigma). 12.5 $\mu$l of HMW standard stock solution were diluted in 500 $\mu$l sample buffer, boiled for 3 minutes and run in a one-well 7.5% polyacrylamide gel as in example II. Electrotransfer to Zeta-probe was done as described by Gershoni and Palade, Anal. Biochem. 1982, 124, 396–405. No methanol was used in the transfer buffer. The blot was washed in $H_2O$ supplemented with 1% TritonX-100, overnight at room temperature. A 4 mm wide vertical strip of the blot was then rinsed in 0.2% TritonX-100 and further incubated with 5 ml of the colloidal iron hydroxide stain prepared as follows:
200 $\mu$l dialysed colloidal iron hydroxide
100 $\mu$l of 10% TritonX-100 in $H_2O$ (v/v)
4.7 ml 0.2M sodium cacodylate/HCl buffer, pH 7 (supplier: BDH Chemicals Ltd. Poole England).
Incubation lasted four hours.

The stained blot was rinsed in $H_2O$ and air-dried. Protein bands detected by the colloidal iron hydroxide stain appeared as brown bands with a very light background.

EXAMPLE IV

Staining of molecular weight markers transferred to a Zeta-probe membrane with colloid gold particles. The staining was carried out with colloidal gold particles, 20 nm mean diameter (supplier: Janssen Life Sciences Products, Beerse, Belgium. HMW standards and Zeta-probe were the same as in example III. The protein blot used for staining was similarly made as in example III. The blot was washed with excess water, overnight at room temperature.

A 4 mm wide vertical strip of the blot was further incubated with 5 ml of the colloidal gold stain prepared as follows:

4 ml colloidal gold sol
1 ml 10% w/v myristyltrimethyl-ammonium bromide.
 The pH adjusted to 8 with NaOH.
 Incubation lasted four hours.

The stained blot was rinsed in $H_2O$ and air-dried. Protein bands detected by this colloidal gold stain appeared as red bands with a light pink background. The sensitivity was comparable with that obtained with the colloidal iron hydroxide on Zeta-probe (example III).

EXAMPLE V

Staining of molecular weight markers transferred to a Zeta-probe membrane with colloidal iron hydroxide particles, followed by hydrolysis with hydrochloric acid and transformation to turnbull's blue with potassium ferrocyanide $[K_4Fe(CN)_6]$.

A strip stained with colloidal iron hydroxide was prepared according to example III. After the completion of the incubation in colloidal iron hydroxide, the strip was washed several times in water, and then treated with the following solution for about 60 seconds:

2 parts HCl 1N,
2 parts water
1 part $K_4Fe(CN)_6$, 0.05M

This solution was made freshly. The strip was rinsed with several changes of water and air-dried. Protein bands detected by this staining procedure appeared as blue bands against a light blue background. The visibility of the proteins was enhanced considerably and the sensitivity now approached that obtained with colloidal gold stain on nitrocellulose blots.

EXAMPLE VI

Staining of Proteins in Cellulose Acetate Membranes

A. Electrophoretic Separation

Cellogel was stored in 30% methanol and dried before use. The membrane was washed in electrophoresis buffer containing 1.34 g Veronal and 10.3 g Veronal-sodium per 1000 ml (pH 8.6). The samples, consisting of 3 µl horse-serum, diluted with electrophoresis buffer to respectively ½, 1/10 and 1/100, were loaded with a microapplicator. Electrophoretic separation was performed at 200 V (maximum intensity 10 MA) for 35 minutes.

B. Staining

Duplicate gels were stained with either amido black or a colloidal gold stain identical with the one described in Example I.

1. Amido black staining

The membranes were stained by contacting them for 30 minutes with a solution containing 0.5 g amido black in 50 ml methanol, 40 ml water and 10 ml of acetic acid. De-staining was carried out during 15 minutes with a mixture of 500 ml methanol, 100 ml acetic acid and 400 ml water.

2. Gold staining

The membrane was fixed for 30 minutes in a mixture of 50 ml methanol, 40 ml water and 10 ml acetic acid. It was then washed three times for 15 minutes with phosphate buffered saline (PH 7.6). Subsequently, the membrane was incubated in the gold stain until staining was saturated (about 2 hours).

C. Results

With amido black, the usual protein staining pattern was obtained. In the 1/100 diluted sample, only a weak staining of the albumin band could be detected.

With the gold stain, the protein bands stained purplish-red. In the 1/100 diluted sample, all the major protein bands were still visible. After drying, the bands turned black.

It appeared that the gold stain is at least 50 times more sensitive than amido black.

EXAMPLE VII

Procedure for Detection of Nucleic Acids Fixed on Nylon Based Membranes, Using Staining with a Colloidal Iron Hydroxide Stain Nucleic acids (DNA or RNA) are applied directly onto the filters (dot blot) or can be transferred after separation in agarose gels, using the Southern (Southern E., Methods in Enzymology, 68 (1979) p.152) or Northern (Thomas, P. S., Proc. Natl. Acad. Sci. USA 77, (1980) p.520) technique. Subsequently, the nucleic acids are fixed on the membranes by heating them at 80° C. for one hour. If the "dot blot" technique for DNA is used, the filter may be treated with denaturing solution (0.5M NaOH, 1.5M NaCl) and neutralised with 3M NaAc solution (pB 5,8) prior to the heating step. For transfers from gels (Southern or Northern) denaturation of the nucleic acids is routinely done in the gel, prior to transfer. After the heating step, the membranes are briefly washed with 0.2% Tween 20 (two times; 5 minutes) and subsequently incubated. with gentle agitation in a suspension of colloidal iron hydroxide (1 hour). This suspension was prepared exactly as described for the staining of proteins. The nucleic acids are detected as yellow-brownish spots or bands, depending on the way of application on the membrane. Subsequently, the filters are washed extensively with water (three times, 5 minutes) and dried. It is also possible to use the reaction with $K_4FE(CN)_6$ as described for protein staining. In that case, the yellow-brownish color is converted into bright blue, resulting in higher sensitivity.

It bas been shown that this staining of nucleic acids, prior to hybridization does not interfere with the subsequent hybridization results.

What we claim is:

1. A kit for use in staining proteins or nucleic acids, comprising a staining suspension consisting essentially of a sol of iron hydroxide in a medium adjusted to an appropriate concentration and an appropriate pH, and supplemented with at least one substance which promotes specific binding of the iron hydroxide to proteins and nucleic acids and, further comprising a ferrocyanide salt complex for modifying or enhancing a signal originating from the staining suspension.

* * * * *